United States Patent [19]

Manning et al.

[11] 4,002,173
[45] Jan. 11, 1977

[54] DIESTER CROSSLINKED POLYGLUCAN HYDROGELS AND RETICULATED SPONGES THEREOF

[75] Inventors: James H. Manning, Monroe; John H. Stark, Campbell Hall, both of N.Y.

[73] Assignee: International Paper Company, New York, N.Y.

[22] Filed: Apr. 14, 1975

[21] Appl. No.: 568,030

Related U.S. Application Data

[63] Continuation-in-part of Ser. No. 490,968, July 23, 1974, abandoned.

[52] U.S. Cl. .................................. 128/296; 424/28; 424/180; 536/112; 536/1; 536/110; 536/119
[51] Int. Cl.² ............................................ F23L 3/00
[58] Field of Search ............ 260/234, 234 R, 209 D

[56] References Cited
UNITED STATES PATENTS 3,871,892    3/1975    Hijiya et al. ................... 260/234 R

OTHER PUBLICATIONS

Chem. Abstracts, vol. 83, 1975, p. 126 parag. 30267y.

*Primary Examiner*—Lewis Gotts
*Assistant Examiner*—Cary Owens

[57] ABSTRACT

Novel hydrogel compositions of diester crosslinked polyglucans and a process for their preparation are provided. Amylose, dextran, and pullulan succinates and glutarates when crosslinked as described were found to not only have use as general fluid sorbants but also to have exceptional hemostatic activity, adherence to a wound, and bioabsorption without causing undue irritation of the tissue or toxic effects. Reticulated hydrogel sponges made of the crosslinked diesters which are particularly useful as general fluid sorbants, and those of amylose succinate and amylose glutarate are most excellent bioabsorbable hemostatic agents. The sponges are made by lyophilizing water-soluble salts of the mono- or half-esters, such as water-soluble salts of amylose succinate or amylose glutarate, under process conditions of the invention in the presence of a reticulating agent which causes a controlled melting of the salt solution as it nears the dry state during the lyophilizing step. The resulting reticulated, porous, open-celled sponge is then crosslinked by heating the sponge under dehydrating conditions to form diester-cross-links. The sponge is highly porous, is moderately strong, and has the ability to retain up to 40 times its weight of isotonic saline. When neutralized with physiologically acceptable salts, the sponge has exceptional hemostatic activity, adherence to bleeding tissue, and bioabsorption without causing substantial irritation of the tissue or toxic effects.

The invention also comprises a process of providing hemostasis at the site of a wound, employing the diester cross-linked polyglucan hydrogels or reticulated sponges thereof.

40 Claims, 4 Drawing Figures

DIESTER CROSSLINKED POLYGLUCAN HYDROGELS AND RETICULATED SPONGES THEREOF

This application is a continuation-in-part of our co-pending application, Ser. No. 490,968, filed July 23, 1974, now abandoned.

BACKGROUND OF THE INVENTION

The present invention relates to novel compositions of matter and to methods of producing them, and more particularly, to novel hydrogel powders and reticulated hydrogel sponges of diester crosslinked polyglucans of succinic or glutaric acid which are capable of not only absorbing large amounts of fluid, but also have excellent adherence and hemostatic activity when applied to bleeding tissue. The invention also comprises the process of providing hemostasis, employing the compositions of the invention.

A variety of methods has been reported which will produce polyglucan mono- or half-ester succinates and glutarates. For the purposes of this invention, the polyglucan succinates or glutarates may be prepared by any method which results in a completely water-soluble polysaccharide when it has a mono-ester succinate or glutarate degree of substitution above 0.35 in the sodium salt form. (Degree of substitution is the mole ratio of moles of succinate or glutarate per mole of anhydroglucose unit.) We have used both the hot formamide procedure described by Jeanes and Jones [J. Amer. Chem. Society, Vol. 74:6116-7 (1952)] and an adaptation of the aqueous alkaline reaction procedure described in U.S. Pat. No. 2,461,139.

When the polyglucan succinates or glutarates are dried in a prescribed manner, the free acid functions of the mono-ester succinate or glutarate condense with unreacted hydroxyl functions of an adjacent polyglucan molecule, thereby forming diester crosslinks. The product formed is a hydrogel. A product, which has crosslinking to such a degree that the product is water insoluble but swells in water, is termed a hydrogel.

Polyglucan hydrogels have been patented, but heretofore all these hydrogels are diether crosslinked (U.S. Pat. No. 3,208,994 and U.S. Pat. No. 3,042,667). These polyglucan hydrogels cannot be used as bioabsorbable hemostatic agents because they are not biodegradable.

Various types of polyglucans have been marketed for use as bioabsorbable hemostatic agents. The $NO_2$-oxidized cellulose (Oxycel) and $NO_2$-oxidized regenerated cellulose (Surgicel) products are still used for this purpose. These products have several disadvantages, among which are those found in the package insert of these products:

1. They are very acidic and cause delayed wound healing and in extreme cases even tissue necrosis.
2. They are non-uniform in composition because some residue is left after even 30 days and these residues cause tissue inflammation.
3. They do not adhere tenaciously to bleeding tissue.

Cellulose sulfate and carboxymethylcellulose have also been patented as useful for bioabsorbable hemostatic agents (U.S. Pat. Nos. 2,764,159; 2,772,999; 2,773,000; 2,914,444 and 3,122,479). These products are also only effective as used in their acidic form and, hence, cause delayed healing and severe inflammatory response.

Usher's U.S. Pat. No. 3,765,419 discloses the use of amylose acetates having certain degrees of substitution as hemostatic agents. However, these mono-esters cannot form diester crosslinks and do not provide the desirable hemostatic properties of the products of the present invention.

So far as we are aware, no one has heretofore made a polyglucan bioabsorbable hemostatic agent having a neutral pH that has immediate hemostatic activity and is completely and uniformly absorbed by being enzymatically hydrolyzed to natural metabolites of the host organism.

The reticulated porous hydrogels of the present invention comprise a 3-dimensional network of interconnecting strands of diester-crosslinked polyglucan succinate or glutarate, especially of amylose, said strands being substantially free of "windows" or closed cells. Hence, these compositions can be described as "reticulated sponges". These reticulated sponges have the ability, not only to hold water in their interstices, but also the interconnecting strands themselves swell and retain fluids because the diester-crosslinked polyglucan succinate or glutarate are hydrogels. The overall product is, therefore, called a "reticulated, diester-crosslinked polyglucan hydrogel sponge."

When the aqueous solution of amylose succinate or glutarate is lyophilized in a prescribed manner, in the presence of a reticulating agent, the polyglucan succinate or glutarate solution will melt at a particular point in the freeze-dry cycle so that a reticulated sponge results. This is sometimes referred to in the lyophilization art as "melt-back".

Sponges of starch, amylose, algin, gelatin and collagen have been patented as absorbable hemostatic agents. The process of preparing the starch sponge is described in U.S. Pat. No. 2,597,011. U.S. Pat. No. 3,081,181 describes a process for producing amylose sponges. U.S. Pat. No. 3,653,383 discloses a sponge of algin. The process for preparing the gelatin sponge is described in U.S. Pat. Nos. 2,465,357 and 2,899,262. The process for preparing a collagen sponge is described in Canadian Pat. No. 920,754. Sponges of partially hydrolyzed polyacrylonitrile also have been proposed (U.S. Pat. No. 3,709,842). U.S. Pat. Nos. 2,764,159; 2,914,444 and 3,122,479 describe sponges of ethers of starch, inulin or cellulose. Only the gelatin sponge is being commercially used as an absorbable sponge capable of maintaining hemostasis, being marketed under the name, Gelfoam. These absorbable sponges have one or more deficiencies such as inadequate hemostatic activity, lack of adherence to bleeding tissue, or excessive foreign body response on the part of the user.

So far as we are aware, no one has heretofore made an amylose succinate or amylose glutarate reticulated hydrogel sponge structure itself, nor has anyone made a bioabsorbable sponge which has immediate hemostatic activity, has excellent adherence to the bleeding wound, and is completely and uniformly absorbed by being enzymatically hydrolyzed to natural metabolites of the host organism without causing undue irritation of the tissue or toxic effects.

It is, therefore, an object of the present invention to provide hydrogel powders and reticulated sponges of diester crosslinked polyglucan succinates and glutarates and processes for their preparation.

It is another object of the present invention to provide a process for achieving surgical hemostasis by applying said powders to the bleeding wound surface.

It is also an object of the invention to provide bioabsorbable hydrogel powders and reticulated sponges which do not have the disadvantages of the prior art.

It is an important object of the present invention to provide reticulated hydrogel sponges of diester-crosslinked amylose succinates and amylose glutarates and a process for their preparation.

It is another object of the present invention to provide a process for achieving surgical hemostasis by applying said sponges to the bleeding wound surface.

Other objects and advantages will become apparent after reading the following description and claims, taken in conjunction with the appended drawings, in which:

Figure 1:
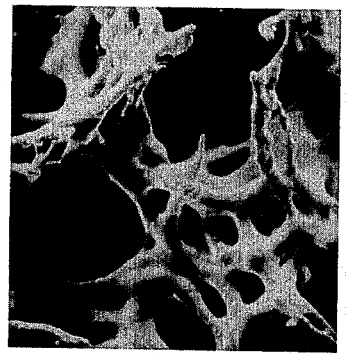
FIG. 1 shows a typical scanning electron micrograph picture of the reticulated hydrogel sponge of amylose succinate of the invention, although not necessarily in accordance with any of the specific examples, in the dry state at a magnification of 145 times.
Figure 3:
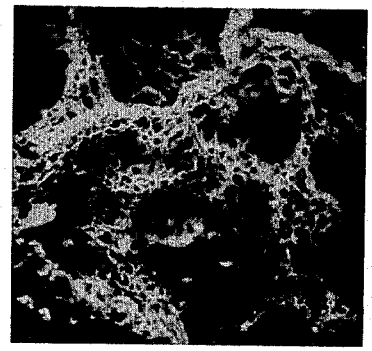

FIG. 3 is another photomicrograph at a magnification of 145 times of a portion of the same sample used in making the photomicrograph of FIG. 1 after it was allowed to swell in water and then freeze-dried, showing that interconnecting strands of diester-crosslinked amylose succinate of the 3-dimensional networks are seen to increase in size and have a microporous structure of their own. Hence, the strands of the sponge are, themselves, hydrogels.

Figure 4:
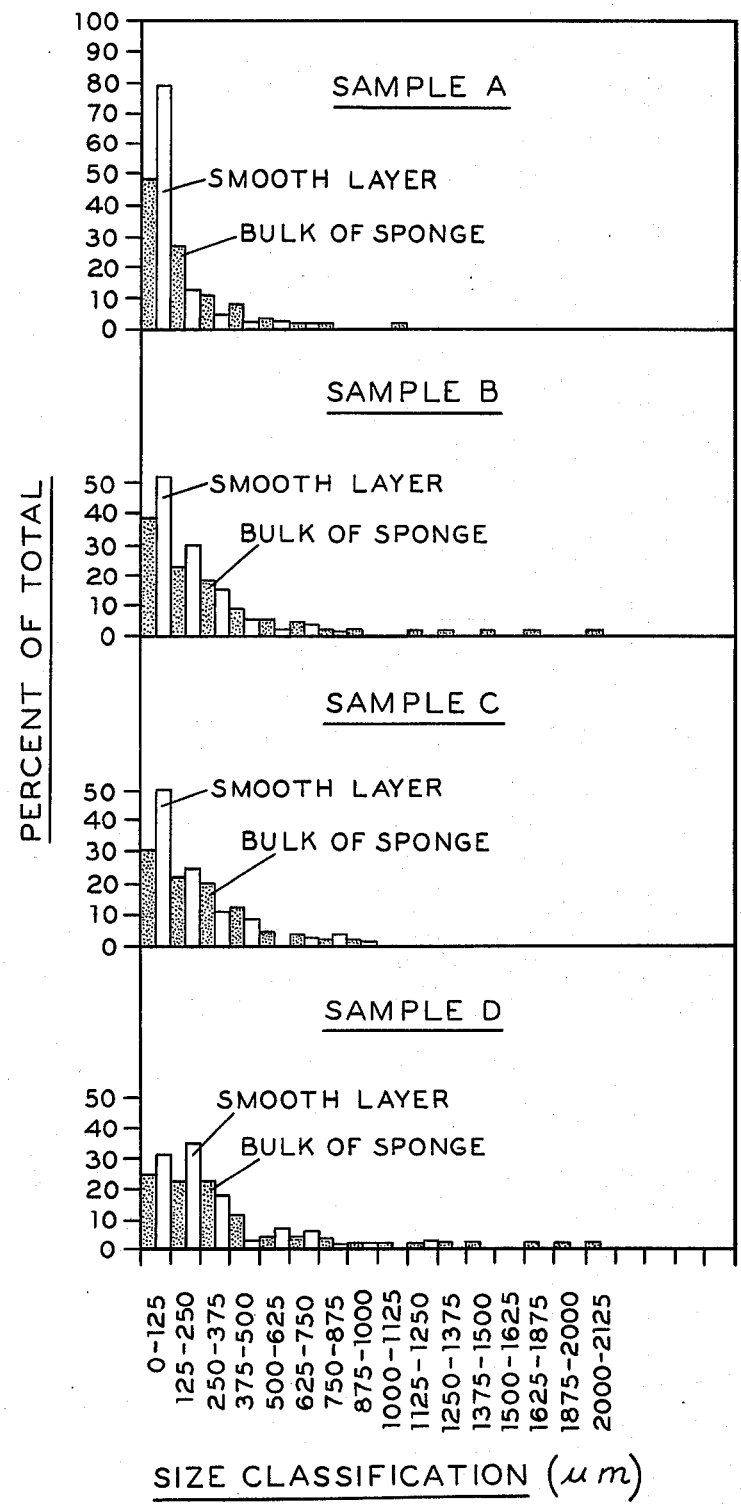

FIG. 4 represents bar graphs of size classifications of four sponges produced in accodance with Example 12.

GENERAL DESCRIPTION OF THE INVENTION

The products of the present invention comprise novel hydrogel diester crosslinked polyglucans, such as amylose, dextran or pullulan, of succinic or glutaric acids. The term "polyglucan" as used in the present specification and in the claims is intended to encompass amylose, pullulan, or dextran, or polymers derived therefrom, having an average molecular weight from approximately 500 up to several million and consisting of glucose residues bonded together mainly by alpha 1-6- or alpha 1-4-glycosidic linkages.

Examples of suitable polyglucans for use in the present invention include amylose, pullulan, and dextran or products obtained by a partial depolymerization of the same. In order to serve as bioabsorbable hemostatic agents, the polysaccharides are preferably linear and alpha-linked glucans.

For most polyglucan polymers, water will be the most suitable solvent for reaction but other liquids having similar solubility properties, such as dimethylsulfoxide, formamide, dimethylformamide, dimethylacetamide, 2-pyrrolidone, or 1-methyl-2-pyrrolidone, will prove suitable under certain circumstances. If desired, solvent mixtures may be used in which water is the main component.

The succinic or glutaric acids are desirably employed as their anhydrides. These anhydrides are both suitable for reaction with a polyglucan and form biodegradable and essentially non-toxic decomposition products.

The steps in the preparation of the diester crosslinked polyglucan hydrogel powders consist of the following:

a. The polyglucan is first made soluble or dissolved in a suitable reaction solvent, i.e., hot formamide, aqueous alkali, or water.

b. The polyglucan is reacted with succinic anhydride or glutaric anhydride to form the corresponding mono-ester. In the case of a reaction conducted in hot formamide, sodium acetate is a suitable catalyst, whereas in water, sodium hydroxide is a suitable catalyst. In aqueous systems, the pH of the reaction is maintained between about 7.0 and 9.0 and temperature between 5° and 25° C. The polyglucan mono-ester should have a Degree of Substitution (D.S.) of between about 0.35 and 2.5, preferably between about 0.8 and 1.2. Products of higher or lower D.S. do not have sufficient sites for diester crosslink formation, or the polyglucan may be insoluble in water.

c. The reaction mixture is filtered to remove any insoluble contaminants.

d. The reaction mixture is dialyzed, or precipitated in an organic solvent, such as into acetone or an aliphatic alcohol or by lowering the pH, to remove undesired salts and low molecular weight by-products.

e. The polyglucan succinate or glutarate monoester is converted to a partial acid form in solution. In the form of the partial acid, partial sodium salt form, the pH is adjusted less than about 5.2, preferably less than about 4.5 and above about 3.8. Preferably, low molecular weight salts formed during pH adjustment are removed by dialysis. The lower level of pH is often dictated by the solubility of the polyglucan mono-ester in the acid form. For example, amylose succinate of D.S. of about 1 is insoluble in water below pH 3.8 and hence, the product is not acidified below 3.8.

f. The partially acidified polyglucan monoester is dried either as a thin film or by spray drying to a powdered non-sticky state preferably with a water content less than 10%.

g. The partially acidified polyglucan monoester is crosslinked by subjecting the product to conditions which essentially remove residual water solvent and allows removal of water formed during diester crosslink formation. In a vacuum oven or in an anhydrous solvent, the temperature may be as low as about 55° C., but preferably a forced air oven above about 105° C. is used to achieve diester crosslinking. The products generally undergo some charring above about 135° C., so this becomes the upper temperature for crosslinking. The time of crosslinking not only depends upon product pH, temperature, vacuum, or air flow and relative humidity, but also upon polyglucan species, degree of mono-ester substitution, and film thickness or particle size. The time of crosslinking is chosen so as to give a water-insoluble product which has the ability to increase its dry weight to about 5 to 90 times, preferably between about 5 and 40 times, of its original weight with isotonic saline when the powder is in the neutral pH sodium salt form. This is known as "Saline Retention" (S.R.). For hemostatic activity, the product desirably should have a Saline Retention (S.R.) of between about 5 and 30, preferably between about 5 and 20.

h. The film is removed from the plate and ground to the desired size by either wet or dry grinding.

i. For maximum sorbing ability, best biotolerability, and suitable stability, the powder product is neutralized with physiologically acceptable salts such as sodium, potassium, magnesium, ammonium, or calcium to have a pH between about 5 and 8. The suitable anions of these salts are succinate, glutarate, acetate, hydroxide, carbonate, bicarbonate or chlorides, or mixtures thereof.

j. For acceptable handling ability, the powders should preferably be ground or spray dried to a particle size greater than about 200 mesh (greater than about 75 microns). The upper size range may be about 50 mesh (about 200 microns), or more, but larger sizes are slower swelling and are more slowly absorbed by the body.

One skilled in the art should realize that, depending upon end use requirements, steps (c) and (d) may be eliminated. Likewise, step (f) could be combined with step (g) as a one-step operation.

As indicated earlier, the preferred products obtained during the reaction process contain molecules of linear polyglucans having both mono-ester and diester functions of succinate or glutarate and their salts bound together by diester bridges which are the common type

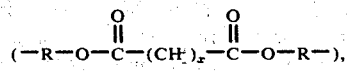

wherein R represents the radicals or residues of the polyglucan substance and x is an integer of 2 or 3.

The preferred gels consist of three dimensional networks of macroscopic dimensions of molecules of polyglucans having mainly alpha-1-6 and alpha-1-4 linkages and derivativized with mono-esters and diesters of succinate and glutarate and their salts, bonded together by ester bridges of the above mentioned type

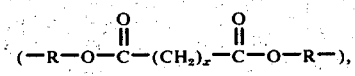

wherein R represents the polyglucan substances and x is an integer of 2 or 3.

The preferred hydrogel products are insoluble in water but are capable of swelling due to the presence of hydroxyl and carboxyl groups and their salts. The capacity of swelling of the hydroxyl product is expressed as a ratio of the weight of the product swollen in isotonic saline to the dry weight of the same powder, and is referred to as its "Saline Retention." The Saline Retention for the neutral sodium salt product produced according to the invention may be from about 5 to 90, preferably from about 5 to 40, but is generally within the range of about 5 to 30, preferably from about 5 to 20.

In the case of preparing the absorbable reticulated sponges of diester-crosslinked polyglucan succinate or glutarate, preferably of amylose succinate or glutarate, the first five steps described hereinabove for producing powders, namely, steps (a) through (e), inclusive, are employed, followed by steps (f) through (k) set forth below:

f. The concentration of the polyglucan succinate or glutarate solution is adjusted to between 2.5% to 7.5% and preferably between 3.0% and 5.0% and the reticulating agent is added. The reticulating agents which we have found most effective are: dimethylsulfoxide, dimethylacetamide, formamide, dimethylformamide, 2-pyrrolidone, and 1-methyl 2-pyrrolidone. Thus, these are the solvents enumerated hereinabove as reaction solvents for the polyglucan polymers. The purpose of the reticulating agent is to cause a controlled melting or "meltback" of the sponge during the freeze-drying process. In order to be effective, the reticulating agent should have the following properties:

1. It should be soluble in water to such an amount that it can lower the freezing point of water enough to cause reticulation to occur.
2. It should have a vapor pressure less than water at the temperatures occurring during lyophilization and at temperatures below about 0° C.
3. At some point in the freeze-dry cycle when the polyglucan succinate or polyglucan glutarate concentration is greater than 20% of the total weight of the remaining composition, the freezing point of the composition should become lower than the product temperature, i.e., the frozen portion melts.
4. The liquid which forms at this point must be a solvent for the polyglucan succinate or polyglucan glutarate, so that the optimum amount of reticulating agent is dependent upon the nature of each specific reticulating agent, the concentration of polyglucan succinate or polyglucan glutarate, concentration of low molecular weight salts, the D.S. of polyglucan succinate or polyglucan glutarate, the solution pH, the salt-type, the thickness of the frozen solution, the heat flux to the bottle contents during freeze drying, the geometry and the diffusion length for water to sublime and condense, and the vacuum within the freeze-dry bottle. Generally about 0.15 to 1.0 parts of reticulating agent per part of polyglucan succinate or polyglucan glutarate are used.

g. The polyglucan succinate or glutarate solution, with reticulating agent, is frozen by having the solution in a bottle rotated in a very cold (less than about −30° C.) bath. If the solution is not frozen quickly with rotation, the ice forms large and irregularly shaped crystals which result in undesirable large and irregular pores in the sponge after lyophilization.

h. The bottle is then subjected to an absolute pressure less than about 1000 microns of mercury so as to cause the contents to undergo lyophilization. In order to cause the desired reticulated sponge structure to form during lyophilization, the vacuum is controlled at some value which depends upon a complex interaction of the specific type of reticulating agent, the concentration of polyglucan succinate or polyglucan glutarate, concentration of low molecular weight salts, the D.S. of the polyglucan succinate or polyglucan glutarate, the solution pH, the salt-type, the thickness of the frozen solution, the heat flux to the bottle during lyophilization, the geometry and the diffusion length for water to sublime and condense, the condenser temperature. Those skilled in lyophilization are familiar with these factors and are aware of how to handle them.

i. After sublimation is complete, the reticulated sponge of polyglucan succinate or polyglucan glutarate is crosslinked by subjecting the sponge to dehydrating conditions which essentially remove the last water solvent and allow removal of water formed during diester-crosslink formation. In a vacuum oven or in an anhydrous solvent, the temperature may be as low as 55° C., but preferably a forced air oven above 105° C. is used to achieve diester-crosslinking. The product generally undergoes some decomposition above 135° C., so this becomes the upper temperature for crosslinking. The time of crosslinking not only depends upon temperature, vacuum, or air flow and relative humidity, but also upon the polyglucan species, degree of mono-ester substitution, product pH, salt-type, concentration of low molecular weight salts, and sponge thickness. The time of crosslinking is chosen so as to give a water-insoluble product which has the ability to increase its dry weight to about 5 to 40 times its original weight with isotonic saline when the sponge is ground into a powder (50 to 100 mesh or 0.30 to 0.15 mm. fraction) which is in the neutral sodium salt form. This number is known as "Saline Retention" (S.R.). For hemostatic activity, the powder desirably should have a Saline Retention (S.R.) of between about 5 and 30, preferably between about 5 and 20. The cross-linked reticulated sponge is flexible when conditioned at 21° C. and 65% relative humidity, of low density and characterized by having most of its pore size less than 1 mm., a void volume between 80 and 95% and an apparent density between 0.30 and 0.075 grams per cubic centimeter.

j. For maximum sorbing ability, best biological tolerability, and suitable stability, the sponge product is neutralized with physiologically acceptable salts such as sodium, potassium, magnesium, ammonium, or calcium to have a pH between about 5 and 8. Suitable anions of these salts are succinate, glutarate, acetate, hydroxide, carbonate, bicarbonate, and chlorides or mixtures thereof.

k. The sponges may be blotted dry until they are used, but preferably the sponges are dried by solvent exchange and air drying.

One skilled in the art should realize that, depending upon end use requirements, steps (c) and (d) may be eliminated in making sponges. Likewise, step (h) could be combined with step (i) as a one-step operation.

Aside from their obvious use as desiccants and sorbents of liquids, the hydrogel powders and sponges produced in accordance with this invention are extremely valuable for absorbable hemostatic sponges. They are capable of achieving hemostasis instantaneously and adhering so tenaciously to the wound that tissue is torn in attempting to dislodge them from the wounded surface. They are completely absorbed in the body without causing substantial inflammatory response or delaying healing or forming toxic products of decomposition. They may, furthermore, be added to other absorbable or nonabsorbable matrices to improve their hemostatic activity. Other purposes of utilization are as disintegrating agents in tablets, as water-keeping laxatives, as agents permitting delayed release of drugs, and as molecular sieving agents.

The preferred reticulated sponge products of the invention are those having an average pore size less than 1 mm., a void volume between about 80 and 95%, preferably between about 90 and 93% and an apparent density between about 0.30 and 0.075 grams per cubic centimeter, preferably between about 0.15 and 0.11 grams per cubic centimeter.

Not only do the sponges of the invention retain water within the interstices of the sponge, but the crossing members themselves swell and imbibe 5 to 40 times their own weight of isotonic saline. These products are, of course, hydrogels.

It has been found that the application of powder to the surface of the sponge which is to be applied against the wound causes certain improvements in the hemostatic action of the product such that the sponge may be removed leaving behind the hemostatic powder only, thus minimizing the total amount of hemostatic material which needs to be left in the body to maintain hemostasis. Relative amounts of between amount 0.1 and 1.0 parts by weight of powder per unit weight of sponge have been found to be particularly satisfactory. For this purpose it is desirable that the powder have an average particle size of between about 200 mesh and 50 mesh (75 microns and 200 microns).

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

Amylose Succinate

Four hundred grams of potato amylose (Superlose, Stein Hall, 9.1% moisture) were sifted into 4000 ml. of rapidly stirred water at 23° C. to give a uniform milky mixture. The mixture was cooled to 10° C. and 595 grams of 50.6% sodium hydroxide plus 1700 ml. of water were added. After the mixture had cleared and the temperature was at 13° C., 685 grams of succinic anhydride powder were sifted into the reaction mixture. After the ph dropped to about 8, a solution of 5 normal sodium hydroxide was added with a dropping funnel (1000 ml. of preweighed solution was used) at a rate sufficient to maintain the pH of the reaction between 8 and 9. The 5 normal sodium hydroxide solution as weighed and the amount used was accurately determined to be 929.8 grams or 788.0 ml. Throughout the reaction, the vessel was cooled to maintain a reaction temperature between 10° and 22° C. The degree of substitution of succinate groups was calculated from the reaction stoichimetry of the equation:

$$\text{Degree of Substitution } (D.S.) = \frac{162 \, (20x - y)}{1000 \, Z}$$

where
$x$ = weight of succinic anhydride in grams.
$y$ = millimoles of sodium hydroxide used.
$Z$ = dry weight of amylose in grams.

$$\text{Hence, } D.S. = \frac{162 \, [20(685) - 11466]}{1000 \, (363.6)}$$

-continued

D.S. = 1.00

On the same day as the reaction was performed, the reaction solution was filtered to remove all particulate matter greater than 5 microns.

The pH of the filtered solution was adjusted to 4.0 with acetic acid. The solution was dialyzed from cellulose tubing to remove low molecular weight salts until the specific conductance of the solution was constant. The solution was concentrated on a flash evaporator to a concentration of 13.2% solids.

A solution of the resulting amylose succinate (13.2% solids, D.S. = 1.00 and pH 4.0) in the partial sodium salt form was cast as a 1 mm. thick film on glass plates. The films were dried at 60° C. for 2 hours in a forced air oven and crosslinked by immediately placing them in a 120° C. forced air oven for about 20 minutes. After cooling, the films and plates were soaked for 15 minutes in a 5% aqueous solution of sodium bicarbonate. The film separated from the plate and was collected on a 0.85 oz. per sq. yd. Cerex (Monsanto Corp.) (unwoven nylon, sometimes referred to as spunbonded nylon) cloth. It was then ground in distilled water in a 1 qt. Waring blender for fifteen seconds at high speed. The pH was adjusted to about 7.0 with aqueous succinic acid solution. The product, which was now a hydrogel powder, was collected on the Cerex cloth and washed twice with 5 times its swollen volume with distilled water. The gel was solvent dried by precipitating into 10 times its swollen volume of anhydrous acetone. The acetone was decanted and the product was dried in a vacuum oven at 60° C. for one hour. The product was lightly crushed in a mortar and pestle to break up aggregates and the resulting powder was screened, successively, on 50, 100 and 200 mesh screens.

The saline retention was determined by swelling 500 mg. of the powder of predetermined moisture content, retained on the 100 mesh screen, in 50 ml. of 0.9% aqueous sodium chloride solution at 23° C. for 10 minutes with stirring. The hydrogel powder was recovered by draining on a preweighed piece of Cerex cloth until it stopped dripping. The wet powder was weighed on the Cerex cloth and the saline retention value was calculated by the equation:

$$\text{Saline Retention } (S.R.) = \frac{\text{wet weight of powder}}{\text{dry weight of powder}}$$

The Saline Retention number was 19.5.

Testing for hemostatic effect was determined by the ability of the material to arrest bleeding resulting from the excision of splenic tissue in an adult dog. The animal was anesthetized using sodium pentobarbital. An abdominal midline incision was made and the spleen externalized. Using curved Mayo dissecting scissors, a portion of the spleen tissue was excised. The area removed was approximately 1 × ⅝ inch, with the depth determined by the curvature of the scissors (approximately ⅛ inch deep). After profuse bleeding was observed, the area was sponged with a dry cotton gauze and immediately a quantity (approximately 300 mg.) of the neutral sodium amylose succinate hydrogel dry powder of this example was put onto the wound and was held for 30 seconds by applying slight pressure on the powder with a dry cellulose gauze sponge. After removal of the gauze sponge, bleeding did not resume and, in fact, most of the powder never was wetted with blood. After 10 minutes of observation, no subsequent bleeding was observed, so the excess powder was removed by addition of isotonic saline to the powder. Most of the powder swelled in the saline solution and was washed away, but the powder which was wet with blood remained at the wound site and maintained hemostasis and became rubbery in consistency. The would could withstand considerable movement and not bleed because the clot had a rubbery consistency and stuck tenaciously to the underlying tissue.

EXAMPLE 2 pH for Cross-linking Films

From a batch of amylose succinate (D.S., 1.0) that was synthesized and purified according to the procedure of Example 1 above, samples were prepared by adjusting the pH to 5.0, 5.2 and 5.5 with sodium bicarbonate solution. Films (1 mm. thick) of these samples were heated at 60° C. for 2 hours and then at 120° C. for 1½ hours in forced air ovens. Very good cross-linking occurred at pH 5.0 and 5.2 as evidenced by the insolubility of the tough film when neutralized in 5% NaHCO₃. The sample at pH 5.5 formed an opaque cream-colored film that dissolved in 5% NaHCO₃ indicating that cross-linking had not taken place.

EXAMPLE 3

Amylose Succinate with a Maximum Degree of Substitution

Amylose succinate was prepared according to the procedure of Example 1, using 30 g. of amylose dissolved in 200 ml. of water, 200 g. of succinic anhydride, 21.1 g. of 50.6% NaOH, and 784.9 g. of 5 normal NaOH. The D.S. of the resulting amylose succinate was 2.43. This product was filtered, dialyzed, and cross-linked according to the procedure of Example 1, except that some films were heated for 22 minutes at 120° C. and others for 35 minutes at 120° C. The S.R. for these samples (100 mesh powders) were 16.0 and 15.6, respectively. These powders (100 mesh) stopped bleeding of a canine spleen wound in less than 30 seconds.

EXAMPLE 4

Salts of Amylose Succinate

The Ca, Mg, K, and NH₄ salts of a cross-linked powder of amylose succinate (D.S., 1.1; S.R., 13.4, prepared according to the general procedure of Example 1) were prepared as follows: Approximately 1.3 g. of the 100 mesh sodium salt form were stirred in 50 ml. of water and acidified with 1 normal HCl to pH 4.0. The gel was washed twice in water (100 ml. each) and then stirred in a 5 wt. percent solution of the particular salt specified in the table below for 4 minutes. The gel was then washed three times in water (100 ml. each), twice in acetone (100 ml. each), and heated under vacuum at 70° C. for 1 hour.

| Salt Ion | Salt Solution Used | S.R. | Hemostasis Rating |
|---|---|---|---|
| Ca | 5% CaCl₂ | 8.1 | Bleeding stopped in less than 30 seconds |
| Mg | 5% magnesium acetate | 11.0 | Bleeding stopped in less than 30 seconds |
| K | 5% potassium acetate | 10.6 | Bleeding stopped in less than 30 seconds |
| NH₄ | 5% ammonium | 10.2 | Bleeding stopped in |

| Salt Ion | Salt Solution Used | S.R. | Hemostasis Rating |
|---|---|---|---|
| | bicarbonate | | less than 30 seconds |

EXAMPLE 5

Dextran Succinate

To 100 g. of dextran in 1 liter of water at 10° C. were added alternately succinic anhydride (100 g.) and 5 normal NaOH (314.8 g.), maintaining the pH between 8 and 9 and the temperature between 6° and 10° C. The D.S. of the resulting dextran succinate was 1.4. This solution of dextran succinate was acidified to pH 4 with glacial acetic acid, dialyzed against distilled water until the specific conductance did not change with time, and concentrated on a flash evaporator at 45°–55° C to 51% solids. One millimeter thick films of the polymer solution were spread on glass plates. Some plates were heated at 60° C. for 2 hours and then at 120° C. for 1 hour, and some heated at 60° C. for 220 minutes and then at 120° C. for 127 minutes. The films were neutralized in 5% sodium bicarbonate solution, ground in 100 ml. of water in a Waring blender for 15 seconds, filtered, and mixed with 600 ml. of water. After the pH of this mixture was adjusted to 7.0 with succinic acid, the ground film was washed two more times in water (600 ml. each) and twice in acetone (400 ml. each), and heated in a vacuum oven at 60° C. for 1 hour. This dry sample was ground in a mortar and pestle and sifted into mesh sizes of 100 (300–150 micrometers), 200 (150–75 micrometers), and greater than 200 (less than 75 micrometers). The S.R. of the 100 mesh sample heated for a shorter time was 85, the S.R. of the 100 mesh sample heated for a longer time was 15.4. Samples of these powders gave good hemostasis on a canine spleen wound stopping bleeding in less than 30 seconds.

EXAMPLE 6

Pullulan Succinate

To 25 g. of pullulan in 225 ml. of water at 10° were added 24.0 g. of 50.6 wt. % NaOH. Succinic anhydride (35 g.) and 5 normal NaOH (53.7 g.) were added alternatively to the pullulan solution according to the procedure of Example 5. The D.S. of the pullulan succinate was calculated as 1.1. This solution of pullulan succinate was worked up into crosslinked powder according to the procedure of Example 5, except that the film was cast from a 36.3% solution heated for 90 minutes at 60° C., and then for 40 minutes at 120° C. The S.R. was 19.9 for 100 mesh powder. A 100 mesh powder sample gave good hemostasis on a canine spleen wound, stopping the bleeding in less than 30 seconds.

EXAMPLE 7

Amylose Glutarate

To 55 g. of amylose in 500 ml. of water at 10° C. were added 25.8 g. of 50.6 wt. % NaOH. Glutaric anhydride (114.1 g.) and 5 normal NaOH (277 g.) were added alternately to the amylose solution according to the procedure of Example 5. The D.S. of the amylose glutarate was calculated as 1.6. This solution of amylose glutarate was worked up into cross-linked powder according to the procedure of Example 5, except that the film was cast from a 27.1% solution heated for 1.5 hours at 60° C. and 25 minutes at 120° C. The S.R. was 14.3. A sample of this powder gave good hemostasis on a canine spleen wound, stopping the bleeding in less than 30 seconds.

EXAMPLE 8

Dextran-Amylose-Succinate

Forty-four grams (52% solids) of uncross-linked dextran succinate prepared in Example 5 were mixed with 156 g. (14.5% solids) of uncross-linked amylose succinate prepared as described in Example 1 using a mechanical stirrer and the pH was adjusted to 4.2 with $NaHCO_3$ solution. A 1 mm. film of this solution was heated at 60° C. for 150 minutes and at 120° C. for 100 minutes and worked up into powder according to the procedure of Example 5. The S.R. was 11.5 on 100 mesh powder. A sample of 100 mesh powder gave good hemostasis, stopping the bleeding in less than 30 seconds on a canine spleen wound.

EXAMPLE 9

Pullulan-Amylose-Succinate

Fifty-six grams (52% solids) of uncross-linked pullulan succinate prepared in Example 6 were mixed with 142 g. (14.5% solids) of amylose succinate according to the procedure for Example 8, except that the film was heated for 35 minutes at 120° C. The S.R. was 16.1 and hemostasis was good, stopping bleeding in less than 30 seconds.

EXAMPLE 10

Amylose Glutarate - Amylose Succinate

Eighty grams (21.7% solids) of uncross-linked amylose glutarate prepared in Example 7 were mixed with 120 g. (14.5% solids) amylose succinate according to the procedure for Example 8, except that the film was heated for 25 minutes at 120° C. The S.R. was 22.8 and hemostasis was good, stopping bleeding in less than 30 seconds.

EXAMPLE 11

Preparation of Amylose Succinate Sponge Using Formamide As a Reticulating Agent Four hundred grams of potato amylose (Superlose, Stein Hall, 12.2% moisture) were sifted into 4700 ml. of rapidly stirred water at 23° C. to give a uniform milky mixture. The mixture was cooled in an ice bath to 10° C. and 1475.3 g. of 4.94 normal sodium hydroxide were added. After the amylose had dissolved and the temperature was at 8° C., 585.0 g. of succinic anhydride power were added to the reaction mixture. After the pH dropped to 7, 4.94 normal sodium hydroxide was added with a dropping funnel (1000 ml. of preweighed solution was used) at a rate sufficient to maintain the pH of the reaction at about 8±1. The sodium hydroxide was added until the solution stabilized at pH 8.5. The remaining sodium hydroxide solution was weighed and the total base used was accurately determined to be 2257.2 g. or 1912.9 ml. Throughout the reaction, the vessel was cooled to maintain a reaction temperature between 8° C. and 20° C. The degree of substitution of succinate groups per anhydroglucose unit was calculated from the reaction stoichiometry using the equation discussed in Example 1:

$$D.S. = \frac{162 [20(585) - 9449.7]}{1000 (351.2)} = 1.04$$

As soon as the reaction was completed, the pH was adjusted to 4.5 with acetic acid and the solution was filtered to remove all particulate matter greater than 5 microns. The filtered solution was then dialyzed to remove low molecular weight molecules. Dialysis was done in a hollow fiber dialysis unit (Bamberg Dialyzer, Asahi Chemical Industries, Japan) against distilled water to a constant specific conductance at a pressure differential of 500 mm. of mercury. The pH of the solution was adjusted to 4.0 during dialysis. The final solution of amylose succinate in the partial sodium salt form at pH 4.0 had a solids content of 5.15%. A portion of this solution (126.2 g. which is equivalent to 6.5 g. of solids) was thoroughly mixed with 2.4 ml. of formamide and enough water to bring the total weight to 160 g. This solution was uniformly frozen on the inside walls of a 1200 ml. Virtis Shell-Freeze flask (Model No. F-128) by rotating the flask and solution horizontally in a dry-ice/acetone bath (−78° C.) until the frozen solution contracted away from the glass walls (accompanied by a loud cracking sound). After removing the flask from the dry-ice/acetone bath, it was immediately slipped into a 10-inch length sleeve of circular knit copper mesh (supplied by Metex Corp., Edison, New Jersey) and the bottle was attached to the manifold of a freeze-drier (New Brunswick Scientific Company, Model No. B66) with an 8 cm. length of 16 mm. inside diameter stainless steel tubing. The pressure was maintained at 600 microns of mercury, measured between the sample and cold trap. The copper mesh provided a more uniform heat flux into the flask during freeze-drying; thus, a more uniform hydrogel sponge product was produced.

The flask was exposed to ambient atmospheric conditions at approximately 24° C. and 50% relative humidity and when possible rotated periodically to partially randomize differences in heat flux from side to side. By freezing a thermocouple probe into the product shell inside the flask, it was found that the bulk of freeze-drying (about 4.5 hours) occurred between −11° C. and −9° C. with a slight drop in temperature to −13° C. just prior to a sharp temperature rise to ambient near completion of freeze-drying. Freeze-drying occurred most rapidly (about 1 hour quicker) at the ends of the flask. The flask was left on the freeze-dryer for several hours after the inside temperature had risen to room temperature.

The sponge was carefully removed from the flask with a spatula, cut open and laid flat, dried at 60° C. for 2 hours in a forced air oven, and immediately cross-linked at 120° C. for 25 minutes in a forced air oven.

The cross-linked sponge was characterized by the following measurements: basis weight, thickness, apparent density, void volume, air flow porosity and saline retention number. All of these measurements were based on a 41.7 square cm. piece of unneutralized sponge conditioned for 48 hours or more at 21° C. and 65% relative humidity, except for the saline retention number. The basis weight was 0.0192 g. per square cm. The thickness, 0.165 cm., was determined as an average of 13 measurements which were made wih a dial-type micrometer with no load on the foot. The apparent density was 0.116 g. per cubic cm. The void volume was based upon an absolute density of the polymer of 1.50 g. per cubic cm. was determined by the fact that a powder made from the foam slowly sank in chloroform (sp. gr. 1.498 g./ml.) and floated in chloroform containing 25% carbon tetrachloride (sp. gr. carbon tetrachloride is 1.595 g./ml.). The void volume was 92.3% as calculated from the formula:

$$\left(1 - \frac{\text{apparent density}}{\text{absolute density}}\right) \times 100 = \% \text{ void volume}$$

The air flow porosity was measured with a Frazier Permeability Machine (Frazier Precision Instrument Company, Gathersburg, Md.) using a special adaptor plate which reduced the sponge area through which the air was pulled to 6.26 square cm. Air flow porosity measurements were made on three areas of the sponge. The average was 829 ft.$^3$/ft.$^2$/min. at 30 inches of mercury, 21° C. and 65% relative humidity.

The saline retention number was determined on a portion of the sample which was dried in a 60° C oven until brittle, gently crushed to a powder and screened to obtain the fraction which passed through a 50 mesh screen and was retained on a 100 mesh screen (0.30 to 0.15 mm.). This fraction was stirred in a 5% solution of sodium bicarbonate (75 ml./g. of powder), collected on a 0.85 oz./yd.$^2$ Cerex cloth and washed three times with 5 times its swollen volume of distilled water. The gel was solvent exchanged with 10 times its swollen volume of anhydrous acetone. The product was dried in a vacuum oven at 60° C. for an hour until dry. Five hundred milligrams of the powder (oven dry weight) was stirred for 10 minutes in 50 ml. of 0.9% sodium chloride solution at 23° C. The swollen powder was recovered by draining on a preweighed piece of Cerex cloth until it stopped dripping. The wet powder was weighed on the Cerex cloth and the saline retention number calculated by the equation shown in Example 1 was found to be 13.25.

For hemostatic testing, the sponge was neutralized by gently stirring it in a 10% solution of calcium acetate (74 ml./g. of sponge) with subsequent addition of a calcium hydroxide slurry until the pH was stabilized for 10 minutes at pH 6.5. The sponge was removed from the solution, gently squeezed to remove excess solution, and washed three times in 1300 ml.-portions of distilled water. Moisture in the damp sponge was solvent exchanged with dry acetone which caused the sponge to shrink to nearly its original size. It was then blotted and allowed to dry between pulp blotters.

The hemostatic properties were determined by the ability of the neutralized sponge to arrest bleeding resulting from the excision of splenic tissue in an adult dog. The animal was anesthetized using sodium phenobarbitol. An abdominal midline incision was made and the spleen externalized. Using curved Mayo dissecting scissors, a portion of the spleen tissue was excised. The area removed was approximately 1 × ⅝ inch, with the depth determined by the curvature of the scissors (approximately ⅛ inch deep). After profuse bleeding was observed, the area was sponged with a dry cotton gauze and immediately a two-ply, 1 × 1.5 inch piece of sponge (approximately 300 ml.) was put onto the would and held for 30 seconds by applying slight pressure on the sponge with a damp cellulose gauze. After removal of the gauze pad, another 30 seconds of pressure was applied if bleeding resumed. The rating was based upon the number of 30-second periods of pressure required. Afrer a minimum of 15 minutes' observation without subsequent bleeding, the sponge was saturated with isotonic saline and physically removed from the wound to assess its adherence characteristics. Only the initial 30-second pressure period was required to maintain hemostasis. It adhered tenaciously to the would withstanding pressure, movement, stretching of the spleen and rubbing.

EXAMPLE 12

Microscopic Characterization of Amylose Succinate Sponges

Figure 2:
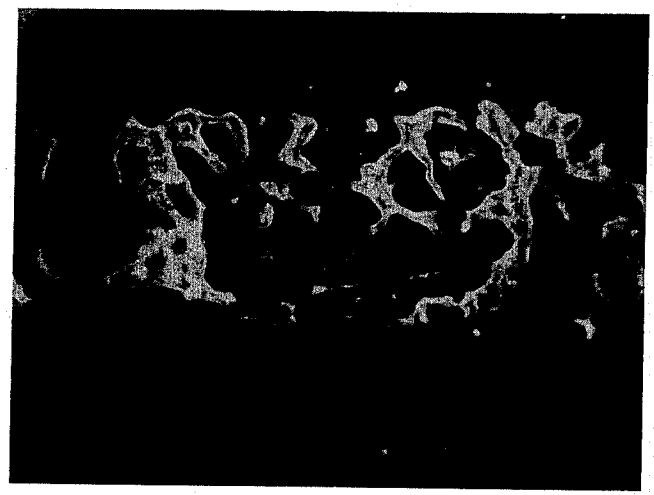
FIG. 2 shows the cross section of a sponge produced in accordance with Example 12, embedded in epoxy resin at a magnification of 52 times.

Six sponges (A-F) were prepared according to Example 11, except that the following amounts of formamide were used; A, none; B, 1.9 ml.; C, 2.2 ml.; D, 2.4 ml.; E, 2.8 ml.; F, 3.2 ml. These sponges ranged from no reticulation (A), very fine in structure (B), to very coarse (F). A comparison of the physical measurements made on these sponges is tabulated below.

tion", shown at a magnification of 52 times in the photomicrograph of FIG. 2 of the appended drawings, was examined in dark field incident light. Various areas of each "cross section" were photographed and enlarged to a total magnification of 160 times. The number of photomicrographs taken varied from 13 to 20 for each of the four samples. A line was drawn on each enlargement passing along and on the cross section of the smooth side of the sponge. Five more lines 1 inch apart were drawn through the thickness of the section and parallel to the plane of the sponge. A metric ruler was laid along each line and the length of each void encountered by the line was measured to the nearest 0.1 cm. (6.25$\mu$m.) Measurements of voids on line 1 (smooth layer — side in contact with the container surface during freeze-drying — generally finer and more closed in structure - see lower surface of cross section shown in FIG. 2) and lines 3, 4 and 5 (combined) representing the bulk of the sponge were tallied in length classes of 2 cm. on the enlargements (125 micrometers in the actual sponge). A percent frequency distribution of

| Sample Number | Basis Weight (g./cm.$^2$) | Thickness (cm.) | Apparent Density (g./cm.$^3$) | Void Volume (%) | Air Flow Porosity (ft$^3$/ft.$^2$/min.) | Saline Retention Number |
|---|---|---|---|---|---|---|
| A[1] | 0.0175 | 0.360 | 0.049 | 96.8 | 0 | 39.07 |
| B[1] | 0.0190 | 0.163 | 0.117 | 92.2 | 469[b] | 19.54 |
| C[c] | 0.0161 | 0.126 | 0.128 | 91.5 | 734 | 15.13 |
| D[1] | 0.0165 | 0.123 | 0.135 | 91.0 | 858[b] | 15.20 |
| E | 0.0150 | 0.105 | 0.143 | 90.5 | 996 | 13.27 |
| F | 0.0190 | 0.130 | 0.146 | 90.3 | 1072 | 12.72 |

[1]based on 100 cm$^2$ piece of sponge
[b]average of 6 measurements at different positions
[c]this sample cannot be neutralized without disintegrating into separate gel particles Samples of sponges B, C, D and E were embedded in epoxy resin. The edges of the embedded sponges were then polished by hand using coarse sandpaper, fine sandpaper, crocus cloth and finally an aqueous paste of alumina (Linde B). The smooth polished "cross sec-void length classes is tabulated below.

| Size Classification (micrometers) | Percent of Total in Central Bulk of Sponge Sample No. | | | | Percent of Total in Smooth Layer of Sponge Sample No. | | | |
|---|---|---|---|---|---|---|---|---|
| | B | C | D | E | B | C | D | E |
| 0–125 | 48.9 | 38.0 | 30.1 | 24.8 | 79 | 52 | 51 | 31 |
| 125–250 | 27.7 | 22.6 | 23.8 | 22.3 | 12 | 30 | 25 | 35 |
| 250–375 | 10.4 | 17.3 | 21.2 | 22.1 | 5 | 9 | 11 | 17 |
| 375–500 | 8.0 | 8.3 | 12.6 | 11.5 | 2 | 5 | 9 | 2 |
| 500–625 | 3.0 | 4.9 | 5.0 | 4.0 | 2 | 1 | — | 7 |
| 625–750 | 1.3 | 3.4 | 3.8 | 4.4 | 1 | 3 | 2 | 5 |
| 750–875 | 0.6 | 1.9 | 1.7 | 3.5 | — | 1 | 3 | 1 |
| 875–1000 | | 1.6 | 0.8 | 1.3 | — | | | 1 |
| 1000–1125 | | — | 0.4 | 1.8 | 1 | | | — |
| 1125–1250 | | 0.4 | | 0.4 | | | | 1 |
| 1250–1375 | | 0.8 | | 0.9 | | | | |
| 1375–1500 | | — | | 0.4 | | | | |
| 1500–1625 | | 0.8 | — | | | | | |
| 1625–1750 | | — | | 0.9 | | | | |
| 1750–1875 | | 0.4 | | 0.4 | | | | |
| 1875–2000 | | 0.4 | | 0.4 | | | | |
| 2000–2125 | | 0.4 | 0.4 | | | | | |

Bar graphs of these data are shown in appended FIG. 4. Data for the smooth side of the sponge is shown not shaded while data for the central bulk of the sponge is shown by surface shading.

The following hemostatic data was obtained using the procedure in Example 11.

| | No. of 30 sec. pressure periods required to attain the hemostasis | Comments on adherence to the wound |
|---|---|---|
| Sample B | 2 | No adherence; blood did not penetrate sponge, but collected underneath forming a soft |

|  | No. of 30 sec. pressure periods required to attain the hemostasis | Comments on adherence to the wound |
| --- | --- | --- |
| Sample D | 1 | clot interface between the sponge and wound. Good adherence. |
| Sample F | 3 | Good adherence, but bled through the large pores when stretched and rubbed. |

EXAMPLE 13

Amylose Succinate Sponge Produced Using Formamide as a Reticulating Agent

The sponge of the example was prepared according to the procedure of Example 11, except that the sample solution which was freeze-dried contained 12.0 g. of solids, 4.0 ml. of formamide and weighed a total of 250 g., instead of 6.5 g., 2.4 ml., and 160 g., respectively.

The following data were obtained for a 100 square cm. piece of sponge:

| | |
| --- | --- |
| basis weight (g./cm.$^2$) | 0.035 |
| thickness (cm.) | 0.260 |
| apparent density (g./cm.$^3$) | 0.135 |
| void volume (%) | 91.0 |
| air flow porosity (ft.$^3$/ft.$^2$/min.) | 595$^a$ |
| saline retention number | 12.74 |

$^a$ = average of 6 measurements

This sponge (in calcium salt form) was tested for hemostatic properties according to the procedure of Example 11. It required two 30-second pressure periods to maintain hemostasis and the adherence to the wound was good, except at the very edges.

EXAMPLE 14

Low D.S. Amylose Succinate Sponge

The sponge of this example was prepared according to the procedure of Example 11, except that less succinic anhydride was used in the reaction to give amylose succinate with a degree of substitution of 0.324 instead of 1.04 and the amount of formamide used to make the sponge was 1.2 ml. instead of 2.4 ml.

The following data were obtained for a 100 square cm. piece of sponge:

| | |
| --- | --- |
| basis weight (g./cm.$^2$) | 0.022 |
| thickness (cm.) | 0.130 |
| apparent density (g./cm.$^3$) | 0.166 |
| void volume (%) | 88.9 |
| air flow porosity (ft.$^3$/ft.$^2$/min.) | 595$^a$ |
| saline retention number | dissolved |

$^a$ = average of 6 measurements

EXAMPLE 15

High D.S. Amylose Succinate Sponge

The sponge of this example was prepared according to the procedure of Example 11, except that more succinic anhydride was used in the reaction to give amylose succinate with a degree of substitution of 2.08 instead of 1.04 and the amount of formamide used was 2.5 ml. instead of 2.4 ml.

The following data were obtained for the sponge:

| | |
| --- | --- |
| basis weight (g./cm.$^2$) | 0.018 |
| thickness (cm.) | 0.133 |
| apparent density (g./cm.$^3$) | 0.138 |
| void volume (%) | 90.8 |
| air flow porosity (ft.$^3$/ft.$^2$/min.) | 850 |
| saline retention number | 15.49 |

This sponge (in calcium salt form) was tested for hemostatic properties according to the procedure of Example 11. It required three 30-second pressure periods to maintain hemostasis and had excellent adherence to the wound.

EXAMPLE 16

Amylose Succinate Sponge Produced Using Formamide as a Reticulating Agent

The hydrogel sponge of this example was prepared according to the procedure of Example 11, except that 2.6 ml. of formamide was used, and the freeze-drying vessel was a teflon-coated aluminum can (dimensions: inside diameter, 8.6 cm.; inside length, 18.5 cm.; wall thickness, 8 mm.) which provided a greater heat flux to the product than occurs in the glass bottles. The top was sealed with a No. 15 rubber stopper and connected to the freeze-dryer with a 9 mm. (inside diameter) tube.

The following data were obtained for a 100 square cm. piece of sponge:

| | |
| --- | --- |
| basis weight (g./cm.$^2$) | 0.021 |
| thickness (cm.) | 0.086 |
| apparent density (g./cm.$^3$) | 0.245 |
| void volume (%) | 83.7 |
| air flow porosity (ft.$^3$/ft.$^2$/min.) | 498$^a$ |
| saline retention number | 11.97 |

$^a$ = average of 6 measurements

This sample of sponge (in calcium salt form) was tested for hemostatic properties according to the procedure of Example 11. It required three 30-second pressure periods to maintain hemostasis and the adherence to the wound was good, except at the edges.

EXAMPLE 17

Amylose Succinate Sponge Produced Using Formamide as a Reticulating Agent

The hydrogel sponge of this example was prepared according to the procedure of Example 11, except that: (1) the solution contained 7.0 g. of solids, 3.0 ml. of formamide and weighed 180 g.; (2) it was frozen on the walls of a teflon-coated aluminum can (dimensions: inside diameter, 8.5 cm.; inside length, 17.5 cm.; wall thickness, 8 mm.) sealed on top with a No. 15 rubber stopper containing a 1 cm. hole in the center; (3) it was freeze-dried in a shelf-type freeze dryer (Virtis Company, Gardiner, New York, Model No. 42-SRC) at 350 to 400 microns of mercury (measured between the cold trap and pump) and a shelf temperature of 93° C.

The following data were obtained for the sponge:

| | |
|---|---|
| basis weight (g./cm.²) | 0.022 |
| thickness (cm.) | 0.187 |
| apparent density (g./cm.³) | 0.115 |
| void volume (%) | 92.3 |
| air flow porosity (ft.³/ft.²/min.) | 763 |
| saline retention number | 12.79 |

EXAMPLE 18

Sponge of Amylose Succinate Produced Using N-Methyl-2-Pyrrolidone as a Reticulating Agent The hydrogel sponge of this example was prepared according to the procedure of Example 11, except that 3.4 ml. of N-methyl-2-pyrrolidone was used as the reticulating agent in place of formamide and enough water was added to bring the total volume of solution to 220 ml.

The following data were obtained for a 100 square cm. piece of sponge:

| | |
|---|---|
| basis weight (g./cm.²) | 0.020 |
| thickness (cm.) | 0.184 |
| apparent density (g./cm.³) | 0.108 |
| void volume (%) | 92.8 |
| air flow porosity (ft.³/ft.²/min.) | 476$^a$ |
| saline retention number | 25.96 |

$^a$ = average of 6 measurements

This sample of sponge was cross-linked an additional 20 minutes at 120° C. to give it enough strength to convert to the calcium salt and test for hemostatic properties according to the procedure of Example 11. It required two 30-second pressure periods and had excellent adherence to the wound.

EXAMPLE 19

Sponge of Amylose Succinate Produced Using Dimethylsulfoxide (DMSO) as a Reticulating Agent The sponge of this example was prepared according to the procedure of Example 11, except that 2.7 ml. of DMSO was used as a reticulating agent in place of formamide.

The following data were obtained for a 100 square cm. piece of sponge:

| | |
|---|---|
| basis weight (g./cm.²) | 0.018 |
| thickness (cm.) | 0.164 |
| apparent density (g./cm.³) | 0.112 |
| void volume (%) | 92.5 |
| air flow porosity (ft.³/ft.²/min.) | 653$^a$ |
| saline retention number | 21.68 |

$^a$ = average of 6 measurements

This sponge (in calcium salt form) was tested for hemostatic properties according to the procedure of Example 11. It required two 30-second periods of pressure to maintain hemostasis and had excellent adherence to the wound.

EXAMPLE 20

Amylose Glutarate Sponge

This sponge of this example was prepared according to the procedure of Example 11, except that amylose glutarate, instead of amylose succinate, was used. The procedure for making the amylose glutarate employed was substantially that of Example 11, except that succinic anhydride was replaced by glutaric anhydride in the amount set forth below along with the other reagents employed in the amounts stated below:

| | |
|---|---|
| Superlose (11.5% moisture) | 55.1 g. |
| water | 500 ml. |
| sodium hydroxide (5 normal), initial addition | 65.0 ml. |
| glutaric anhydride (anhydrous) | 114.1 g. |
| sodium hydroxide (5 normal), add during reaction | 256.3 ml. |
| total NaOH added | (379.2 g.)= 321.3 ml. |

The equation for determining the degree of substitution had to be modified to:

$$D.S. = \frac{162\left(\frac{2000 x}{114.1} - Y\right)}{1000Z}$$

where
x = grams of glutaric anhydride
y = moles of sodium hydroxide used
z = dry weight of amylose in grams $$\text{Hence, } D.S. = \frac{162\left[\frac{2000(114.1)}{114.1} - 5(321.3)\right]}{1000(48.8)} = 1.31$$

The following data were obtained by the resulting sponge:

| | |
|---|---|
| basis weight (g./cm.²) | 0.019 |
| thickness (cm.) | 0.173 |
| apparent density (g./cm.³) | 0.111 |
| void volume (%) | 91.6 |
| air flow porosity (ft.³/ft.²/min.) | 504 |
| saline retention number | 16.67 |

This sample of sponge (in calcium salt form) was tested for hemostatic properties according to the procedure of Example 11. It required two 30-second periods to maintain hemostasis and had excellent adherence to the wound.

EXAMPLE 21

Amylose Succinate Powder on Amylose Succinate Sponge

Cross-linked amylose succinate powder produced according to Example 1 was sprinkled on the surface of a crosslinked amylose succinate sponge produced according to Example 11. The procedure was to spray the sponge with a fine mist of water so that the surface became damp enough for the powder to adhere to it. The powder was then dried on the surface of the sponge by placing it between two pieces of Cerex and drying for about 15 minutes at 50° C. in a forced air oven.

These sponges with powder on one surface were tested for hemostatic activity with the powdered surface on the wound according to the procedure in Example 11. When a 50 to 100 mesh size powder at 10% add on was used, good hemostasis and adherence to the wound were observed. When a 100 to 200 mesh powder was used at 30% add on, hemostasis could be effected and then, after wetting with isotonic saline, the sponge could be removed leaving behind a portion of the powder which maintained hemostasis.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A hydrogel solid comprising diester crosslinked polyglucan selected from the class consisting of amylose, dextran and pullulan succinates and glutarates, said hydrogel solid being water-insoluble and the neutral pH sodium salt of which has a saline retention of isotonic saline solution sufficient to increase the weight of said hydrogel solid to an amount of between about 5 and 90 times its weight.

2. A hydrogel solid according to claim 1, comprising diester cross-linked amylose succinate.

3. A hydrogel solid according to claim 1, comprising diester cross-linked dextran succinate.

4. A hydrogel solid according to claim 1, comprising diester cross-linked pullulan succinate.

5. A hyrogel solid according to claim 1, comprising diester cross-linked amylose glutarate.

6. A hydrogel solid according to claim 1, which, when in the form of its neutral pH sodium salt, has a saline retention of between about 5 and 40 times its original weight.

7. A hydrogel solid according to claim 1, which, when in the form of its neutral pH sodium salt, has a saline retention of between about 5 and 20 times its original weight.

8. A hydrogel solid according to claim 1, which, prior to cross-linking, has a degree of substitution of between about 0.35 and 2.5.

9. A hydrogel solid according to claim 1, which, prior to cross-linking, has a degree of substitution of between about 0.8 and 1.2.

10. A hydrogel solid in accordance with claim 1, in the form of a reticulated porous sponge.

11. A reticulated, porous hydrogel sponge in accordance with claim 10, wherein the polyglucan is amylose.

12. A reticulated, porous hydrogel sponge in accordance with claim 10, having a pH of between about 5 and 8.

13. A reticulated, porous hydrogel sponge in accordance with claim 10, wherein the average pore size is less than about 1 millimeter.

14. A reticulated, porous hydrogel sponge in accordance with claim 10, wherein the void volume is between about 80% and 95%.

15. A reticulated, porous hydrogel sponge in accordance with claim 11, wherein the cross-linked polyglucan diester is of amylose succinate.

16. A reticulated, porous hydrogel sponge in accordance with claim 11, wherein the cross-linked polyglucan diester is of amylose glutarate.

17. A reticulated, porous sponge of diester cross-linked amylose hydrogel selected from the class consisting of succinate and glutarate, said hydrogel being water-insoluble, the neutral pH sodium salt of which has a saline retention of isotonic saline solution sufficient to increase the weight of said hydrogel to an amount of between about 5 and 40 times its weight, having an average pore size of less than about 1 millimeter and a void volume of between about 80% and 95%, having the ability to retain up to 40 times its weight of isotonic saline.

18. A reticulated, porous hydrogel sponge, having applied to at least one surface thereof, a powder of hydrogel solid in accordance with claim 1.

19. A reticulated, porous hydrogel sponge in accordance with claim 18, wherein the amount of powder is between about 0.1 and 1.0 parts per unit weight of sponge.

20. A process for preparing a diester cross-linked polyglucan hydrogel solid according to claim 1, consisting essentially of acidifying to a pH of less than about 5.2 a polyglucan succinate or glutarate mono-ester and removing the water therefrom at a temperature of below about 135° C. to cross-link the monoester and form a diester which is water-insoluble and the neutral pH sodium salt of which has a saline retention of isotonic saline solution sufficient to increase the weight of said hydrogel solid to an amount of between about 5 and 90 times its original weight.

21. A process in accordance with claim 20, wherein the hydrogel solid is cross-linked until it has a saline retention of between about 5 and 40 times its original weight.

22. A process in accordance wih claim 20, wherein the hydrogel solid is cross-linked until it has a saline retention of between about 5 and 20 times its original weight.

23. A process in accordance with claim 20, wherein the polyglucan succinate or glutarate starting material has a degree of substitution of between about 0.8 and 1.2.

24. A process for preparing a reticulated, porous sponge of diester cross-linked polyglucan hydrogel according to claim 1, consisting essentially of acidifying to a pH of less than about 5.2 a polyglucan succinate or glutarate mono-ester having a degree of substitution of between about 0.8 and 1.2, adding a reticulating agent in an amount capable of providing controlled melting during freeze-drying, freezing the resulting mixture at a temperature below about minus 30° C. and freeze-drying under an absolute pressure of less than about 1000 microns of mercury, and finally removing the water therefrom at a temperature of below about 135° C. to cross-link the mono-ester and form a diester which is waterinsoluble and the neutral pH sodium salt of which has a saline retention of isotonic saline solution sufficient to increase the weight of said hydrogel solid to an amount of between about 5 and 40 times its original weight.

25. A process in accordance with claim 24, wherein the hydrogel solid is cross-linked until it has a saline retention of between about 5 and 20 times its original weight.

26. A process in accordance with claim 24, wherein the polyglucan is amylose.

27. A process according to claim 24, wherein the reticulating agent is: (1) of vapor pressure less than water at a temperature below about 0° C., (2) capable of reducing the freezing point of the composition during freeze drying to a point at which the remaining composition melts and (3) in combination with the water remaining, a solvent for the polyglucan succinate or glutarate mono-ester.

28. A process for providing hemostasis at the site of a wound which comprises applying to the surface of the wound a diester cross-linked polyglucan hydrogel solid in accordance with claim 1, having a saline retention of between about 5 and 30 times its original weight.

29. A process in accordance with claim 28, wherein the hydrogel solid, prior to cross-linking, has a degree of substitution of between about 0.35 and 2.5.

30. A process in accordance with claim 28, wherein the hydrogel solid, prior to cross-linking, has a degree of substitution of between about 0.8 and 1.2.

31. A process in accordance with claim 28, in which the polyglucan diester is amylose succinate.

32. A process in accordance with claim 28, in which the polyglucan diester is dextran succinate.

33. A process in accordance with claim 28, in which the polyglucan diester is pullulan succinate.

34. A process in accordance with claim 28, in which the polyglucan diester is amylose glutarate.

35. A process in accordance with claim 28, wherein the diester cross-linked hydrogel is in the form of a reticulated porous sponge.

36. A process in accordance with claim 35, wherein the reticulated porous sponge has an average pore size of less than about 1 millimeter.

37. A process in accordance with claim 35, wherein the reticulated porous sponge has a void volume of between about 80% and 95%.

38. A process for providing homostatis at the site of a wound a powder of hydrogel solid in accordance with claim 1.

39. A process in accordance with claim 38, wherein the amount of powder is between about 0.1 and 1.0 parts per unit weight of sponge.

* * * * *

UNITED STATES PATENT AND TRADEMARK OFFICE
CERTIFICATE OF CORRECTION

PATENT NO. : 4,002,173
DATED : January 11, 1977
INVENTOR(S) : James H. Manning et al.

It is certified that error appears in the above-identified patent and that said Letters Patent are hereby corrected as shown below:

Column 3, line 37, delete "accodance" and replace with -- accordance --.

Column 5, formula at line 30 should read:

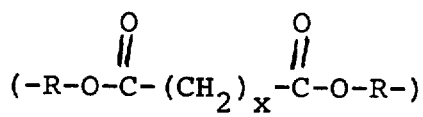

$$(-R-O-\overset{O}{\overset{\|}{C}}-(CH_2)_x-\overset{O}{\overset{\|}{C}}-O-R-)$$

Column 8, line 51, change "as" to -- was --.

Column 11, line 14, "1.4" should read -- 1.14 --.

Column 11, line 44, delete "10°" and replace with -- 10°C. --.

Column 13, line 66, delete "wih" and replace with -- with --.

Column 14, line 2, delete "was" and replace with -- as --.

Column 14, line 66, delete "would" and replace with -- wound --.

Column 15, line 3, delete "afrer" and replace with -- after --.

Column 15, line 9, delete "would" and replace with -- wound --.

UNITED STATES PATENT AND TRADEMARK OFFICE
CERTIFICATE OF CORRECTION

PATENT NO. : 4,002,173
DATED : January 11, 1977
INVENTOR(S) : James H. Manning et al.

It is certified that error appears in the above-identified patent and that said Letters Patent are hereby corrected as shown below:

Column 16, in column "C" of table (first occurrence), in next to last line, delete "0.4" and replace with -- – --.

Column 16, in column "D" of table (first occurrence), in last line, delete "0.4" and delete "–" above it.

Column 16, in column "E" of table (first occurrence), in fifth line from bottom, insert -- – --; and insert "0.4" in last line.

Claim 38, line 1, "homostatis" should be -- hemostasis --.

Signed and Sealed this

Seventeenth Day of May 1977

[SEAL]

Attest:

RUTH C. MASON
Attesting Officer

C. MARSHALL DANN
Commissioner of Patents and Trademarks